United States Patent
Grashow et al.

(10) Patent No.: US 10,589,048 B2
(45) Date of Patent: Mar. 17, 2020

(54) MODULAR BACK STRAP FOR PATIENT INTERFACE DEVICE

(71) Applicant: KONINKLIJKE PHILIPS N.V., Eindhoven (NL)

(72) Inventors: Jonathan Sayer Grashow, Pittsburgh, PA (US); Robert William Baiko, Pittsburgh, PA (US)

(73) Assignee: Koninklijke Philips N.V., Eindhoven (NL)

(*) Notice: Subject to any disclaimer, the term of this patent is extended or adjusted under 35 U.S.C. 154(b) by 851 days.

(21) Appl. No.: 15/034,879

(22) PCT Filed: Oct. 20, 2014

(86) PCT No.: PCT/IB2014/065462
§ 371 (c)(1),
(2) Date: May 6, 2016

(87) PCT Pub. No.: WO2015/068067
PCT Pub. Date: May 14, 2015

(65) Prior Publication Data
US 2016/0271354 A1    Sep. 22, 2016

Related U.S. Application Data

(60) Provisional application No. 61/902,406, filed on Nov. 11, 2013.

(51) Int. Cl.
*A61M 16/06* (2006.01)
*A61M 16/00* (2006.01)

(52) U.S. Cl.
CPC .... *A61M 16/0683* (2013.01); *A61M 16/0057* (2013.01); *A61M 16/0622* (2014.02)

(58) Field of Classification Search
CPC ........ A61M 16/06–0694; A62B 18/02; A62B 18/025; A62B 18/084
See application file for complete search history.

(56) References Cited

U.S. PATENT DOCUMENTS

| | | | | |
|---|---|---|---|---|
| 1,706,601 A | * | 3/1929 | Drager | A62B 18/084 128/207.11 |
| 2,353,643 A | * | 7/1944 | Bulbulian | A62B 18/084 128/207.11 |

(Continued)

FOREIGN PATENT DOCUMENTS

| | | |
|---|---|---|
| GB | 203741 | 9/1923 |
| JP | 1991111813 U | 12/1991 |

(Continued)

*Primary Examiner* — Valerie L Woodward
(74) *Attorney, Agent, or Firm* — Michael W. Haas

(57) ABSTRACT

A back strap for a patient interface device having a headgear component including a first strap member and a second strap member attached to the first strap member and structured to wraparound a back of the patient's head. The back strap member includes a first portion having a first attachment mechanism structured to couple the first portion to the second strap member, a connecting portion extending from the first portion, and a second portion having a second attachment mechanism structured to couple the second portion to at least one of the first strap member, a patient sealing assembly, or skin, hair, neck or clothing of the patient in a manner wherein the back strap member is configured to hold the second strap member and prevent it from riding up on a head of the patient during use.

12 Claims, 10 Drawing Sheets

(56) References Cited

U.S. PATENT DOCUMENTS

| | | | |
|---|---|---|---|
| 5,517,986 A * | 5/1996 | Starr | A61M 16/06 128/201.23 |
| 5,542,128 A * | 8/1996 | Lomas | A61M 16/0683 128/207.11 |
| 6,805,117 B1 | 10/2004 | Ho | |
| 7,878,200 B2 * | 2/2011 | Zollinger | A61M 16/0633 128/201.22 |
| 7,900,630 B2 * | 3/2011 | Geiselhart | A61M 16/06 128/205.25 |
| 2008/0264422 A1 | 10/2008 | Fishman | |
| 2010/0000534 A1 * | 1/2010 | Kooij | A61M 16/0666 128/204.18 |
| 2010/0031963 A1 | 2/2010 | Lee | |
| 2010/0229286 A1 | 9/2010 | Ahlgren | |
| 2011/0197341 A1 | 8/2011 | Formica | |
| 2012/0024290 A1 | 2/2012 | Amarasinghe | |

FOREIGN PATENT DOCUMENTS

| | | |
|---|---|---|
| WO | WO9720597 A1 | 6/1997 |
| WO | WO2010073142 A1 | 7/2010 |
| WO | WO2013050920 A1 | 4/2013 |
| WO | WO2013064930 A1 | 5/2013 |

\* cited by examiner

MODULAR BACK STRAP FOR PATIENT INTERFACE DEVICE

CROSS-REFERENCE TO RELATED APPLICATIONS

This patent application claims the priority benefit under 35 U.S.C. § 371 of international patent application no. PCT/IB2014/065462, filed Oct. 20, 2014, which claims the priority benefit under 35 U.S.C. § 119(e) of U.S. Provisional Application No. 61/902,406 filed on Nov. 11, 2013, the contents of which are herein incorporated by reference.

BACKGROUND OF THE INVENTION

1. Field of the Invention

The present invention pertains to patient interface devices structured to deliver a flow of breathing gas to a patient, and, in particular, to patient interface devices employing a headgear component having a modular back strap to improve performance.

2. Description of the Related Art

There are numerous situations where it is necessary or desirable to deliver a flow of breathing gas non-invasively to the airway of a patient, i.e., without intubating the patient or surgically inserting a tracheal tube into the patient's esophagus. For example, it is known to ventilate a patient using a technique known as non-invasive ventilation. It is also known to deliver positive airway pressure (PAP) therapy to treat certain medical disorders, the most notable of which is OSA. Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, a nasal cushion that rests beneath the patient's nose (such as a "pillows" style nasal cushion having nasal prongs that are received within the patient's nares or a "cradle" style nasal cushion that rests beneath and covers the patient's nares), or a full face mask that covers the patient's face. Such patient interface devices may also employ other patient contacting components, such as forehead supports, cheek pads and chin pads. The patient interface device is connected to a gas delivery tube or conduit and interfaces the ventilator or pressure support device with the airway of the patient, so that a flow of breathing gas can be delivered from the pressure/flow generating device to the airway of the patient.

It is known to maintain such devices on the face of a wearer by a headgear having one or more straps adapted to fit over/around the patient's head. One popular patient interface device 2 is shown in FIGS. 1 and 2. As seen in FIGS. 1 and 2, patient interface device 2 includes a nasal mask 4 for providing a seal and delivering a breathing gas to the patient's airway, and a headgear apparatus 6 for securing patient interface device 2 to the patient's head. Headgear apparatus 6 includes a first strap 8 that extends from nasal mask 4 at the patient's nose to the crown of the patient's head and a second strap 10 which attaches to first strap 8 above the ear and wraps around the back of the patient's head/neck.

Patient interface devices like patient interface device 2 are extremely appealing to patients due to their minimal size and straps. Because of this, patients will very often initially choose a device of this type, but will experience problems with second strap 10 riding up on the back of the head while they are asleep. Such riding often results in patient interface device 2, and in particular nasal mask 4, becoming dislodged from the face as shown in FIG. 2. In many cases, the patient will then request a new patient interface device with a different headgear configuration. This costs the supplier a new patient interface device and requires someone, such as a respiratory therapist, to take time to fit the patient with a completely different device.

In addition, the forces applied to nasal mask 4 by this type of headgear apparatus may be less than optimal because nasal cushions such as nasal cushion 4 typically work better when the forces applied to the nose bridge and upper lip can be adjusted independently to achieve proper cushion orientation with respect to the face. Having another strap for the mask 4 is adventitious not only for the initial adjustment, but it also aids in helping stabilize the mask while the patient is sleeping. Without the addition of a stabilization strap the mask could become dislodged during sleep thus causing interruptions to therapy delivery.

SUMMARY OF THE INVENTION

In one embodiment, a back strap is provided for a patient interface device having a headgear component including a first strap member and a second strap member attached to the first strap member and structured to wrap around a back of the patient's head. The back strap member includes a first portion having a first attachment mechanism structured to couple the first portion to the second strap member, a connecting portion extending from the first portion, and a second portion having a second attachment mechanism structured to couple the second portion to at least one of the first strap member, a patient sealing assembly (the faceplate or cushion thereof) or the skin, hair, neck or clothing of the patient in a manner wherein the back strap member is configured to hold the second strap member and prevent it from riding up on a head of the patient during use.

DETAILED DESCRIPTION OF EXEMPLARY EMBODIMENTS

Figure 1:
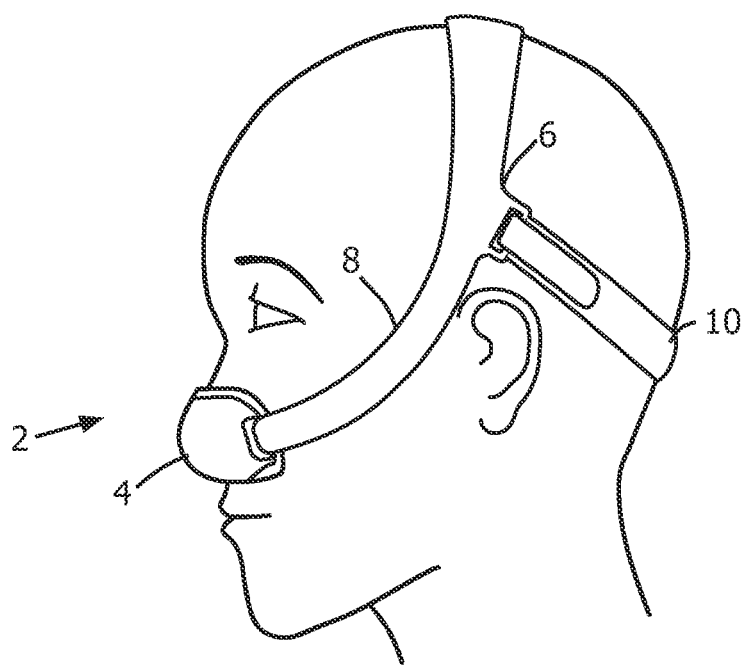
FIGS. 1 and 2 are schematic diagrams of a prior art patient interface device including a prior art headgear.
Figure 2:
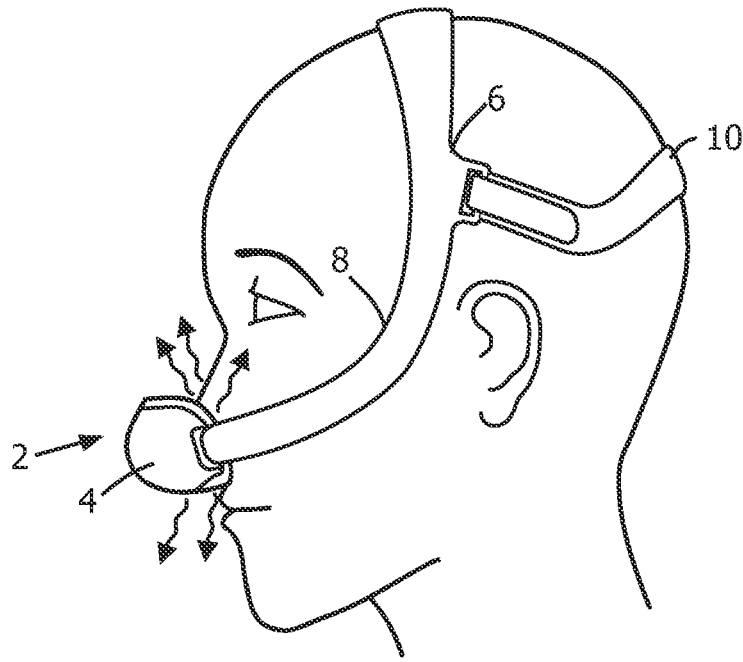

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As used herein, the term "textile" shall mean a material consisting of a network of interlaced or otherwise entangled natural or artificial fibers made by, for example and without limitation, weaving, knitting, spreading, crocheting, or bonding (e.g., by chemical, mechanical, heat or solvent treatment) the fibers to form the network, and may include, for example, and without limitation, woven and nonwoven fabric materials.

As used herein, the term "foam" shall mean a substance that is formed by trapping pockets of gas or compressible particles in a solid material, and may include closed-cell foams wherein the gas forms discrete pockets each completely surrounded by the solid material, and open-cell foams, wherein the gas pockets connect with each other.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 3:
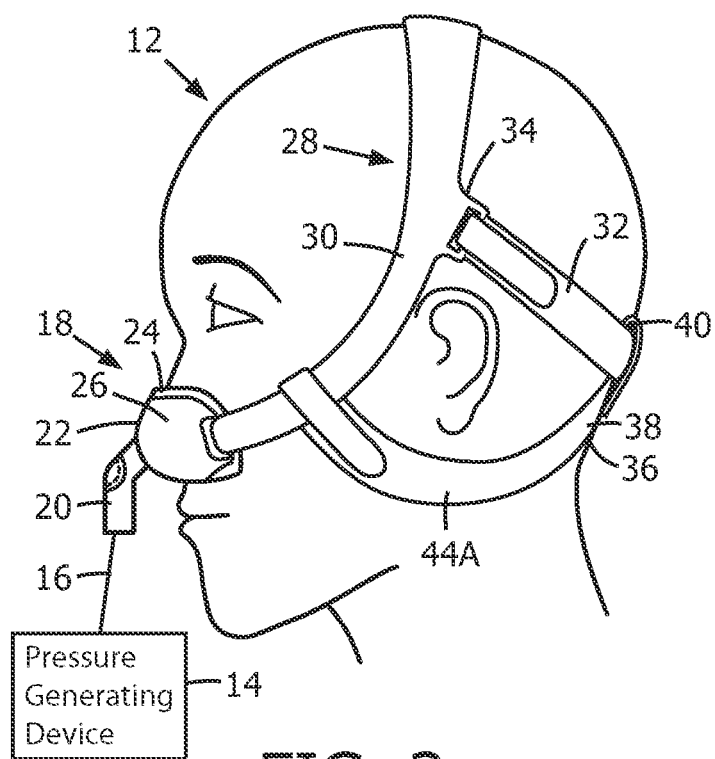
FIGS. 3 and 4 are schematic diagrams of a system adapted to provide a regimen of respiratory therapy to a patient according to one exemplary embodiment.
Figure 4:
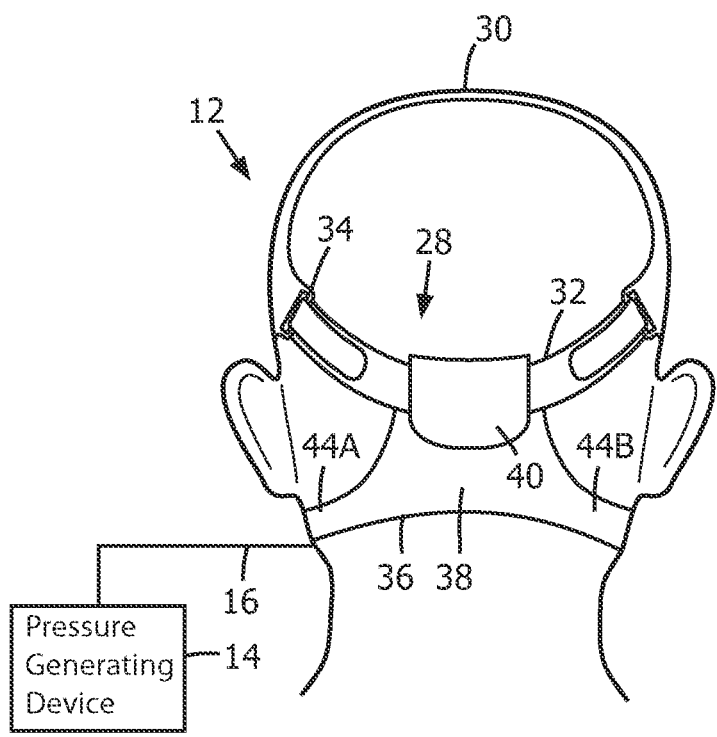

A system 12 adapted to provide a regimen of respiratory therapy to a patient according to one exemplary embodiment is generally shown in FIGS. 3 and 4. System 12 includes a pressure generating device 14, a delivery conduit 16, and a patient interface device 18 having a fluid coupling conduit 20. Pressure generating device 14 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 16 is structured to communicate the flow of breathing gas from pressure generating device 14 to patient interface device 18 through fluid coupling conduit 20, which in the illustrated embodiment is an elbow connector. Delivery conduit 16 and patient interface device 18 are often collectively referred to as a patient circuit.

In the exemplary embodiment, patient interface device 18 includes a patient sealing assembly 22, which in the illustrated embodiment is a nasal mask. However, other types of patient sealing assemblies, such as, without limitation, a nasal/oral mask, a nasal cushion, or a full face mask, which facilitate the delivery of the flow of breathing gas to the airway of a patient, may be substituted for patient sealing assembly 22 while remaining within the scope of the present invention. Patient sealing assembly 22 includes a cushion member 24 coupled to a faceplate member 26. In the illustrated embodiment, cushion member 24 is defined from a unitary piece of soft, flexible, cushiony, elastomeric material, such as, without limitation, silicone, an appropriately soft thermoplastic elastomer, a closed cell foam, or any combination of such materials. Also in the illustrated embodiment, faceplate member 26 is made of a rigid or semi-rigid material, such as, without limitation, an injection molded thermoplastic or silicone. An opening in faceplate member 26, to which fluid coupling conduit 20 is coupled, allows the flow of breathing gas from pressure generating device 14 to be communicated to an interior space defined by cushion member 24, and then to the airway of a patient.

Patient interface device 18 also includes a headgear component 28 for securing patient interface device 18 to the patient's head. Headgear component 28 includes a first strap member 30 that extends from each side of faceplate member 26 at the patient's nose to the crown of the patient's head and a second strap member 32 which attaches to first strap member 30 above the ear and wraps around the back of the patient's head/neck. In one exemplary embodiment, first strap member 30 is made of a semi-rigid material such as, without limitation, silicone or another suitable polymer. In an alternative exemplary embodiment, first strap member 30 is made of a more flexible material, such as, without limitation, a foam laminate material that includes: (i) a middle foam layer made of, for example, a resiliently stretchable open-celled polyurethane foam, (ii) an outer textile layer made of, for example, a resiliently stretchable loop fabric, such as a blend of nylon and spandex, and (iii) an inner textile layer made of, for example, a resiliently stretchable wicking fabric, such as a blend of polyester and spandex.

Also in the exemplary embodiment, second strap member 32 is made of a foam laminate material as just described and attaches to first strap member 30 by a hook and loop fastening system provided thereon. In particular, each end of second strap member 32 may be threaded through respective looped portions 34 provided on opposites sides of first strap member 30 and then be bent back on itself in order to adhere the hook fastener portion to the loop fastener portion and thereby adjustably connect second strap member 32 to first strap member 30. It will be understood that the described hook and loop fastening arrangement is meant to be exemplary only, and that other selectively adjustable fastening arrangements, such as snaps, buttons, adhesive, etc., are also possible within the scope of the present invention.

Figure 5:
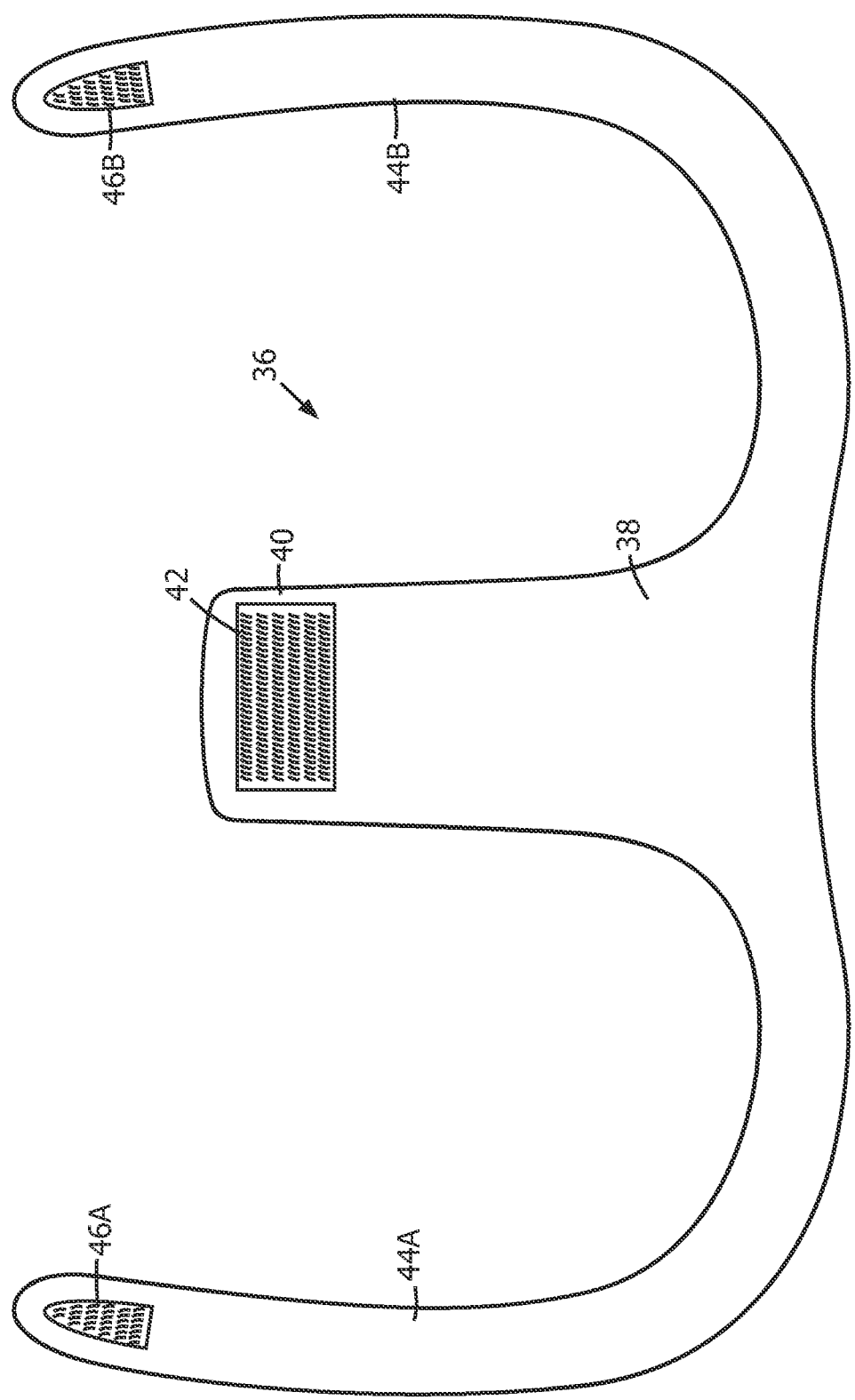
FIG. 5 is a front elevational view of a back strap member according to the exemplary embodiment forming a part of a patient interface device of the system of FIGS. 3 and 4.

In addition, headgear component 28 further includes a back strap member 36 that, as seen in FIGS. 3 and 4, is structured to run under the ears of the patient from each end of first strap member 30 and connect to second strap member 32 at the back of the head/neck. FIG. 5 is a front elevational view of back strap member 36 according to the exemplary embodiment. As seen in FIG. 5, back strap member 36 includes a central portion 38 having a tab member 40 extending therefrom. The front surface of tab member 40 is provided with a hook pad 42. Back strap member 36 also includes first and second side strap members 44A and 44B that extend from opposite sides of central portion 38. In the exemplary embodiment, first and second side strap members 44A and 44B each have an arcuate shape. The front surface of each of first and second side strap members 44A and 44B is provided with a respective hook pad 46A, 46B.

In the exemplary embodiment, back strap member 36 is made of a foam laminate material as described elsewhere herein. It will be understood, however, that this is meant to be exemplary only and that other materials may also be used, such as fabric, silicone (or another rubber-like material), a thermoplastic, or some combination thereof.

In operation, back strap member 36 is attached to and made part of headgear component 28 by threading tab member 40 under second strap member 32 and then bending tab member 40 back on itself in order to adhere hook pad 42 to a loop fastener portion provided on the front surface thereof, which in the exemplary embodiment is provided by the outer textile layer of the foam laminate (e.g., a resiliently stretchable loop fabric). First and second side strap members 44A and 44B are then each threaded under an end of first strap member 30 adjacent patient sealing assembly 22 and then bent back on itself in order to adhere hook pad 46A, 46B to a loop fastener portion provided on the front surface thereof, which in the exemplary embodiment is provided by the outer textile layer of the foam laminate (e.g., a resiliently stretchable loop fabric). When so attached, back strap member 36 will hold second strap member 32 in place and prevent it from moving/riding up on the back of the head while the patient sleeps. In addition, it will be understood that the described hook and loop fastening arrangement is meant to be exemplary only, and that other selectively adjustable fastening arrangements, such as snaps, buttons, adhesive, etc., are also possible within the scope of the present invention.

Figure 17:
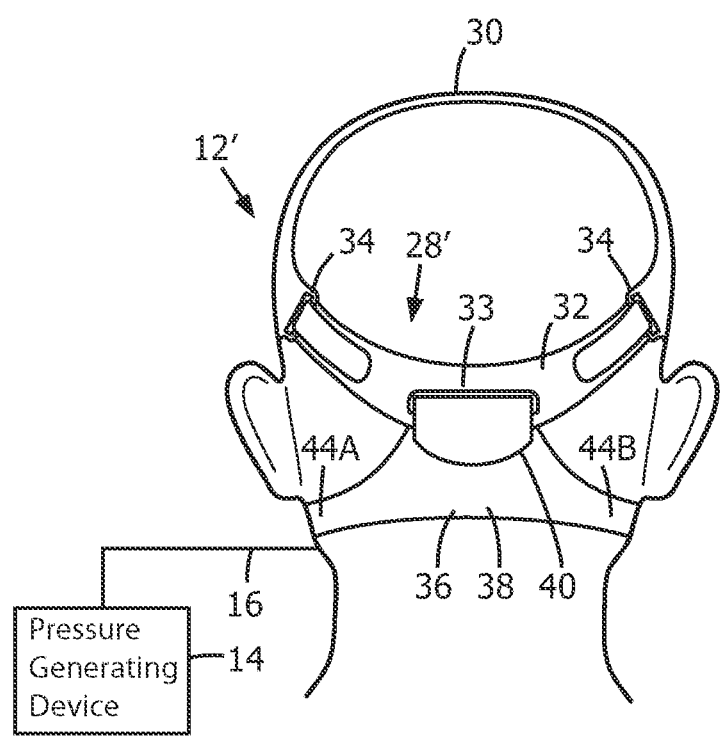
FIG. 17 is a schematic diagram of a system adapted to provide a regimen of respiratory therapy to a patient according to an alternative exemplary embodiment.

FIG. 17 is a schematic diagram of an alternative system 12' adapted to provide a regimen of respiratory therapy to a patient that is similar to system 12. System 12', however, employs an alternative headgear component 28' wherein second strap member 32 has a slit 33 provided therein through which tab member 40 may be threaded as shown in FIG. 17. A main benefit of having slit 33 is that it will prevent movement of tab member 40 across the back of the head.

Figure 6:
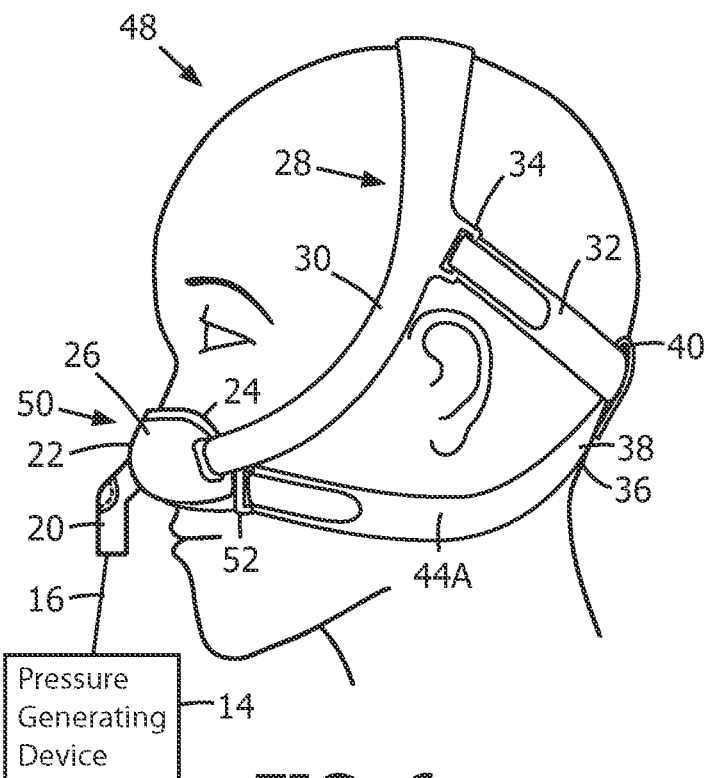
FIG. 6 is a schematic diagram of a system adapted to provide a regimen of respiratory therapy to a patient according to an alternative exemplary embodiment

FIG. 6 is a schematic diagram of a system 48 adapted to provide a regimen of respiratory therapy to a patient according to an alternative exemplary embodiment. System 48 is similar to system 12, and like components are labeled with like reference numerals. However, as seen in FIG. 6, system 48 includes an alternative patient interface device 50 wherein first and second side strap members 44A and 44B of back strap member 36, rather than being threaded under an end of first strap member 30, are instead directly attached to respective loop member 52 provided on and extending from faceplate member 26 (or, alternatively, cushion member 24). This configuration is advantageous since it provides additional sealing forces to the cushion member 24.

Figure 7:
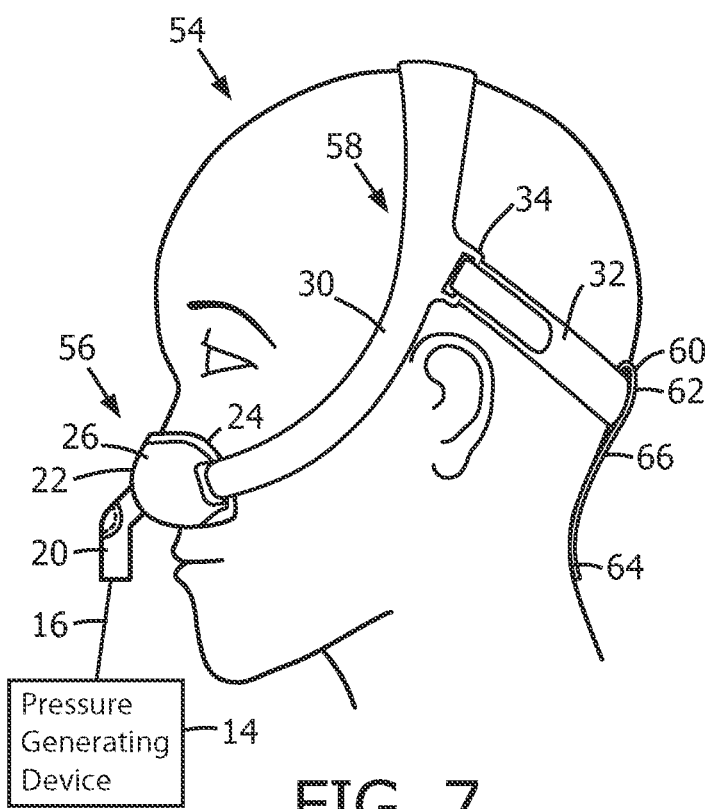
FIGS. 7 and 8 are schematic diagrams of a system adapted to provide a regimen of respiratory therapy to a patient according to another alternative exemplary embodiment.
Figure 8:
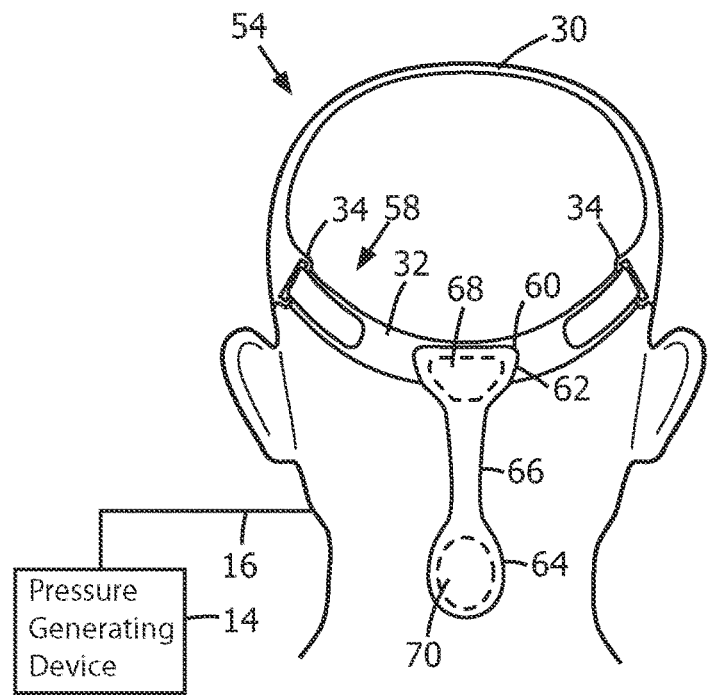

FIGS. 7 and 8 are side and rear schematic diagrams of a system 54 adapted to provide a regimen of respiratory therapy to a patient according to a further alternative exemplary embodiment. System 54 is similar to system 12, and like components are labeled with like reference numerals. However, system 54 includes an alternative patient interface device 56 that employs an alternative headgear component 58. As seen in FIGS. 7 and 8, headgear component 58 is similar to headgear component 28 as it includes first strap member 30 and second strap member 32. However, headgear component 58 includes an alternative back strap member 60 described below to hold second strap member 32 in place and prevent it from moving/riding up on the back of the head while the patient sleeps.

Figure 9:
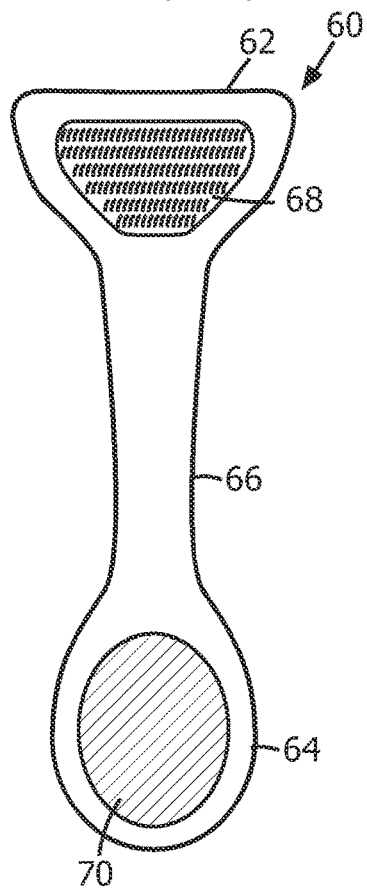
FIG. 9 is a front elevational view of a back strap member according to another exemplary embodiment forming a part of a patient interface device of the system of FIGS. 7 and 8.

FIG. 9 is a front elevational view of back strap member 60 according to the exemplary embodiment. Back strap member 60 includes a top attaching portion 62, a bottom attaching portion 64 and a connecting portion 66 provided in between top attaching portion 62 and bottom attaching portion 64. In the exemplary embodiment, back strap member 60 is made of a foam laminate material as described elsewhere herein. It will be understood, however, that this is meant to be exemplary only and that other materials may also be used, such as fabric, silicone (or another rubber-like material), a thermoplastic, or some combination thereof. In addition, as seen in FIG. 9, the front surface of top attaching portion 62 is provided with a hook pad 68, and the front surface of bottom attaching portion 64 is provided with an adhesive pad 70 made of an adhesive material such as silicone gel or polyurethane gel.

In operation, back strap member 60 is attached to and made part of headgear component 58 by coupling hook pad 68 to a loop fastener portion provided on second strap member 32, which in the exemplary embodiment is provided by the outer textile layer of the foam laminate (e.g., a resiliently stretchable loop fabric). It will be understood, however, that the described hook and loop fastening arrangement is meant to be exemplary only, and that other selectively adjustable fastening arrangements, such as snaps, buttons, adhesive, etc., are also possible within the scope of the present invention. Adhesive pad 70 is then releasably attached to the hair, skin and/or clothing of the patient as shown in FIGS. 7 and 8. When so attached, back strap member 60 will hold second strap member 32 in place and prevent it from moving/riding up on the back of the head while the patient sleeps.

Figure 10:
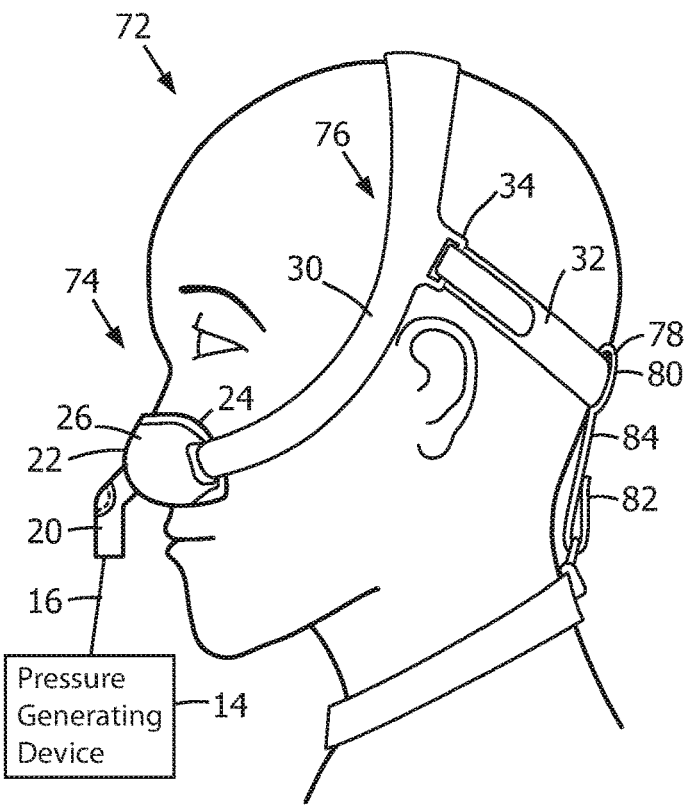
FIGS. 10 and 11 are schematic diagrams of a system adapted to provide a regimen of respiratory therapy to a patient according to yet another alternative exemplary embodiment.
Figure 11:
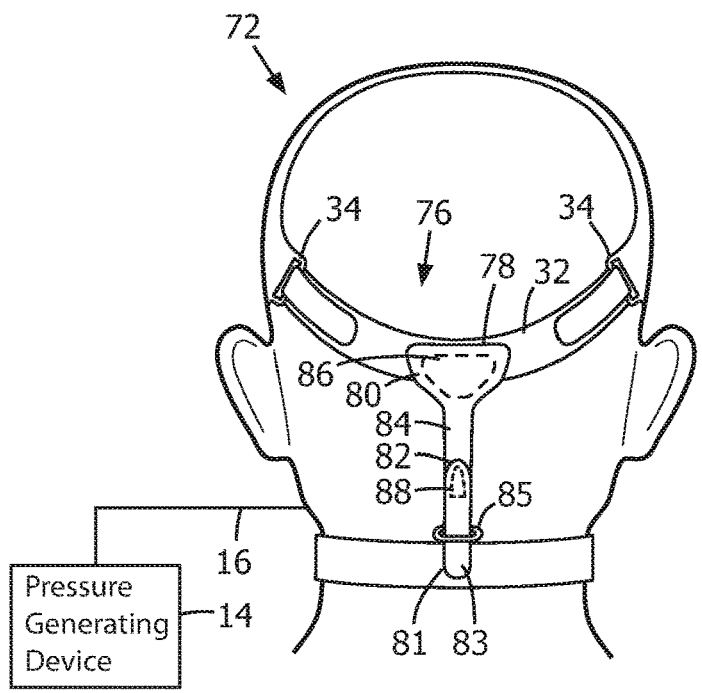

FIGS. 10 and 11 are side and rear schematic diagrams of a system 72 adapted to provide a regimen of respiratory therapy to a patient according to still a further alternative exemplary embodiment. System 72 is similar to system 12, and like components are labeled with like reference numerals. However, system 72 includes an alternative patient interface device 74 that employs another alternative headgear component 76. As seen in FIGS. 10 and 11, headgear component 76 is similar to headgear component 28 as it includes first strap member 30 and second strap member 32. However, headgear component 76, includes an alternative back strap member 78 described below to hold second strap member 32 in place and prevent it from moving/riding up on the back of the head while the patient sleeps.

Figures 12, 13:
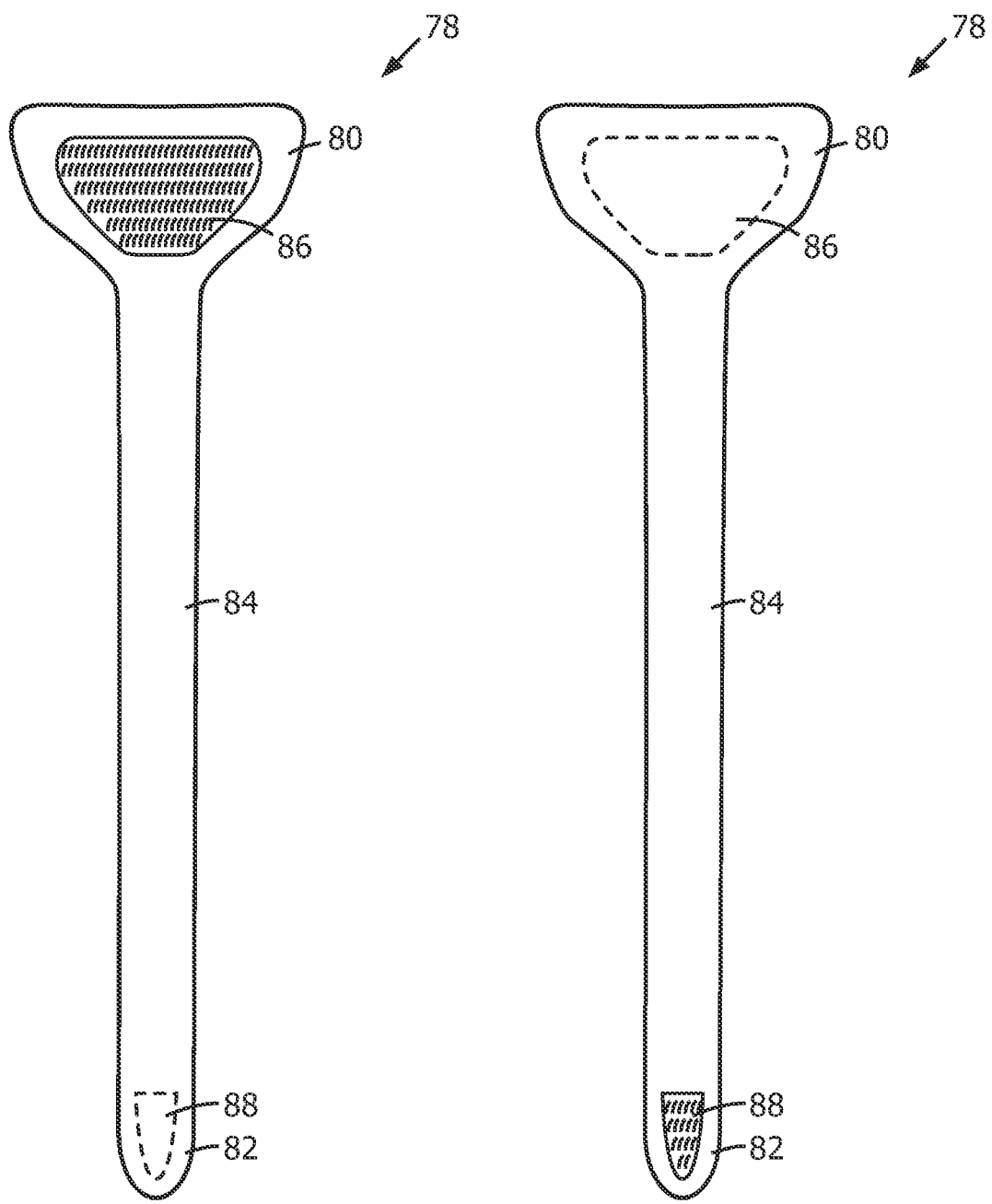
FIG. 12 is a front elevational view and FIG. 13 is a rear elevational view of a back strap member according to another exemplary embodiment forming a part of a patient interface device of the system of FIGS. 10 and 11.

FIG. 12 is a front elevational view and FIG. 13 is a rear elevational view of back strap member 78 according to the exemplary embodiment. Back strap member 78 includes a top attaching portion 80, a bottom attaching portion 82, and a connecting portion 84 provided in between top attaching portion 80 and bottom attaching portion 82. In the exemplary embodiment, back strap member 78 is made of a foam laminate material as described elsewhere herein. It will be understood, however, that this is meant to be exemplary only and that other materials may also be used, such as fabric, silicone (or another rubber-like material), a thermoplastic, or some combination thereof. In addition, as seen in FIG. 12, the front surface of top attaching portion 80 is provided with a hook pad 86, and the rear surface of bottom attaching portion 82 is provided with a hook pad 88.

Headgear component 76 further includes a clip member 81 having a biased portion 83 structured to be selectively connected to the patient's clothing, and a looped portion 85 extending from biased portion 83.

In operation, back strap member 78 is attached to and made part of headgear component 76 by coupling hook pad 86 to a loop fastener portion provided on second strap member 32, which in the exemplary embodiment is provided by the outer textile layer of the foam laminate (e.g., a resiliently stretchable loop fabric). Bottom attaching portion 82 is then inserted through looped portion and bent back on itself as shown in FIGS. 7 and 8 to attach hook pad 88 to a loop fastener portion provided on the surface thereof. When so attached, back strap member 78 will hold second strap member 32 in place and prevent it from moving/riding up on the back of the head while the patient sleeps. Further, it will be understood that the described hook and loop fastening arrangement is meant to be exemplary only, and that other selectively adjustable fastening arrangements, such as snaps, buttons, adhesive, etc., are also possible within the scope of the present invention.

Figure 14:
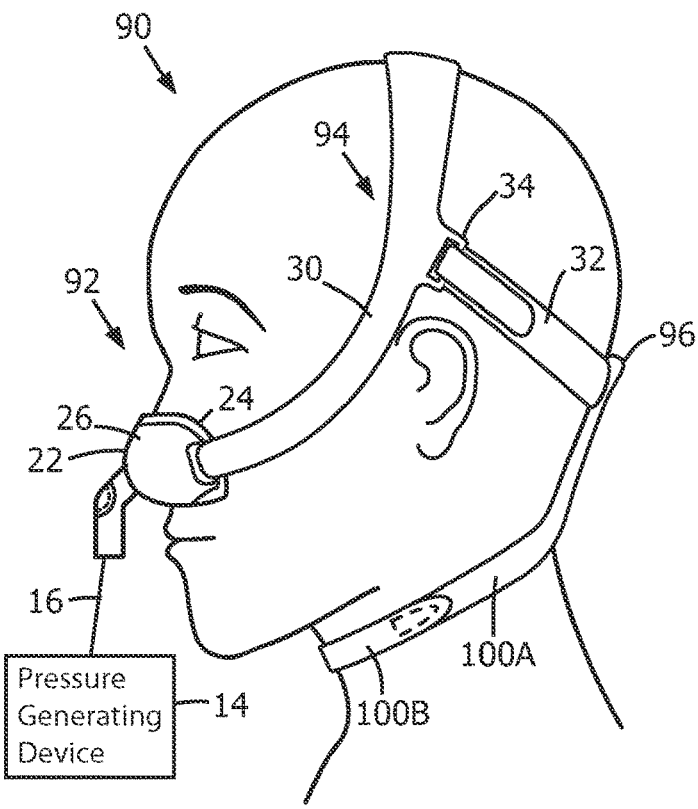
FIGS. 14 and 15 are schematic diagrams of a system adapted to provide a regimen of respiratory therapy to a patient according to still another alternative exemplary embodiment.
Figure 15:
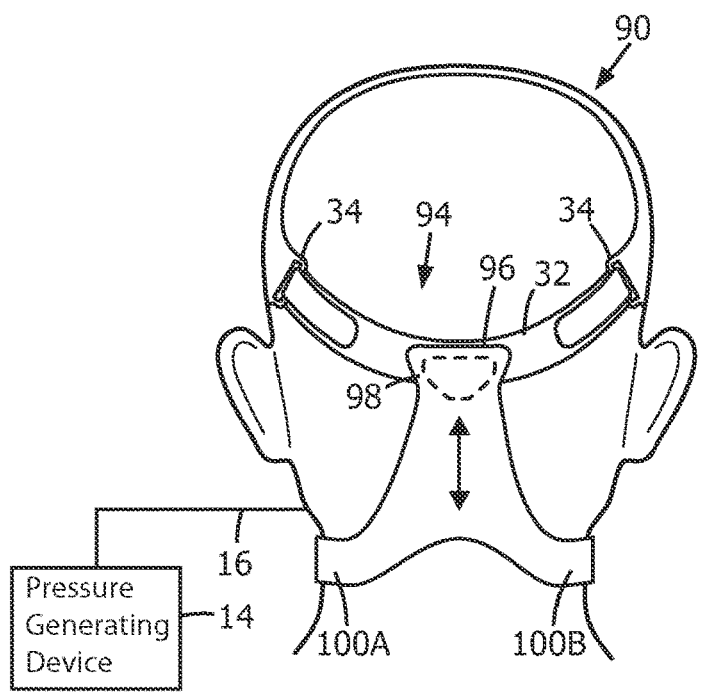

FIGS. 14 and 15 are side and rear schematic diagrams of a system 90 adapted to provide a regimen of respiratory therapy to a patient according to another further alternative exemplary embodiment. System 90 is similar to system 12, and like components are labeled with like reference numerals. However, system 90 includes yet another alternative patient interface device 92 that employs yet another alternative headgear component 90. As seen in FIGS. 14 and 15, headgear component 94 is similar to headgear component 28 as it includes first strap member 30 and second strap member 32. However, headgear component 94 includes another alternative back strap member 96 described below to hold second strap member 32 in place and prevent it from moving/riding up on the back of the head while the patient sleeps.

Figure 16:
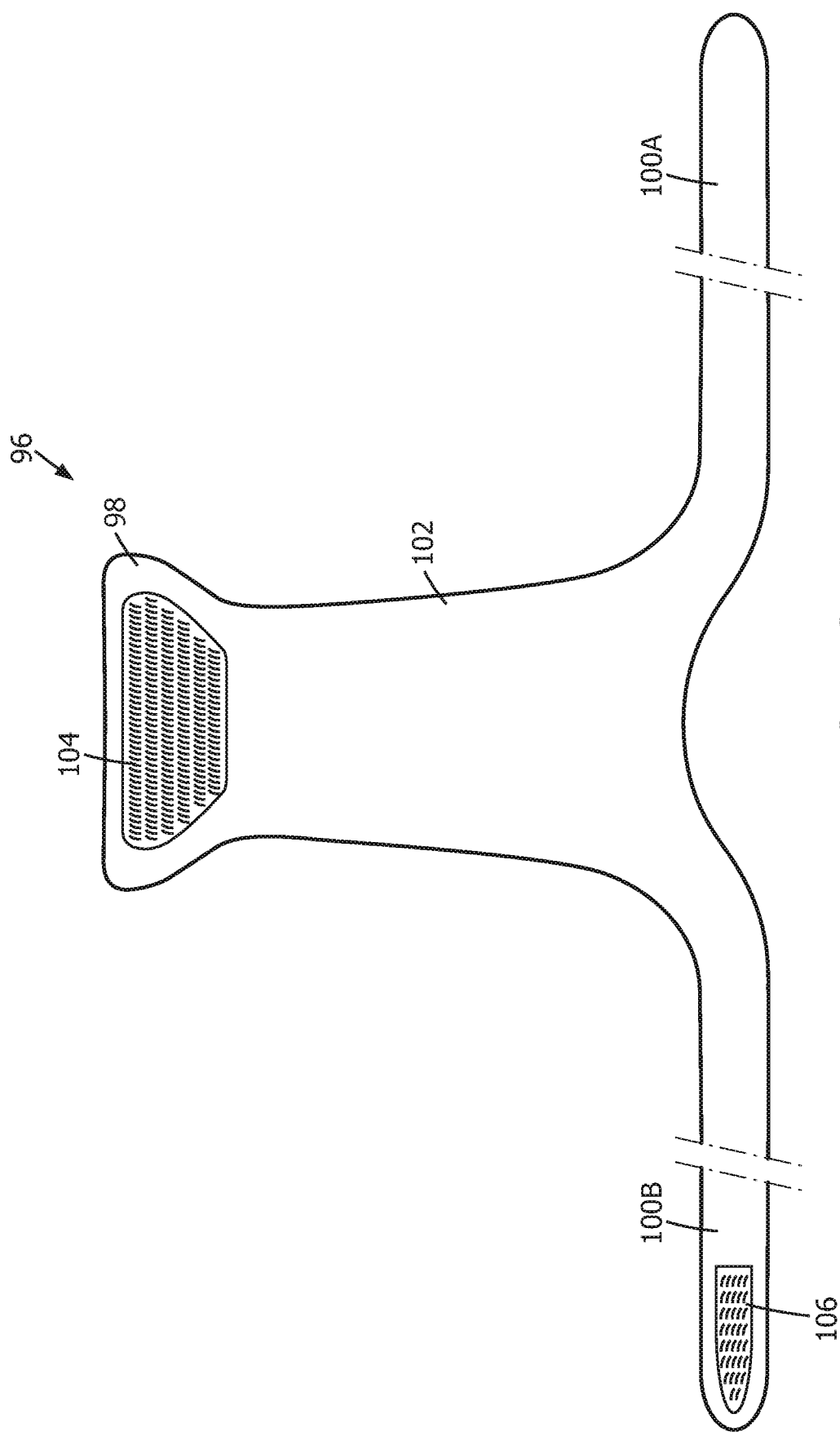
FIG. 16 is a front elevational view of a back strap member according to another exemplary embodiment forming a part of a patient interface device of the system of FIGS. 14 and 15.

FIG. 16 is a front elevational view of back strap member 96 according to the exemplary embodiment. Back strap member 96 includes a top attaching portion 98, bottom attaching straps 100A and 100B, and a connecting portion 102 provided in between top attaching portion 98 and bottom attaching straps 100A and 100B. In the exemplary embodiment, back strap member 96 is made of a foam laminate material as described elsewhere herein. It will be understood, however, that this is meant to be exemplary only and that other materials may also be used, such as fabric, silicone (or another rubber-like material), a thermoplastic, or some combination thereof. In addition, as seen in FIG. 16, the front surface of top attaching portion 98 is provided with a hook pad 104, and the end of the front surface of bottom attaching strap 100B is provided with a hook pad 106.

In operation, back strap member 96 is attached to and made part of headgear component 94 by coupling hook pad 104 to a loop fastener portion provided on second strap member 32, which in the exemplary embodiment is provided by the outer textile layer of the foam laminate (e.g., a resiliently stretchable loop fabric). Bottom attaching straps 100A and 100B are then wrapped around the neck of the patient as shown in FIGS. 14 and 15 and hook pad 106 is attached to a loop fastener portion of bottom attaching strap 100A, which in the exemplary embodiment is provided by the outer textile layer of the foam laminate (e.g., a resiliently stretchable loop fabric). When so attached, back strap member 96 will hold second strap member 32 in place and prevent it from moving/riding up on the back of the head while the patient sleeps. It will be understood that the described hook and loop fastening arrangement is meant to be exemplary only, and that other selectively adjustable fastening arrangements, such as snaps, buttons, adhesive, etc., are also possible within the scope of the present invention.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A headgear component for a patient interface device structured to deliver a flow of breathing gas to a patient, comprising:
   a first strap member having a first end structured to extend from a first side of a patient sealing assembly of the patient interface device and a second end structured to extend from a second side of the patient sealing assembly opposite the first side of the patient sealing assembly, the first strap member having a central portion structured to extend over a crown of the patient's head when the headgear component is donned by the patient;
   a second strap member having a first end attached to the first end of the first strap member and a second end attached to the second end of the first strap member, the second strap member being structured to wrap around a back of the patient's head when the headgear component is donned by the patient, the second strap member having a middle portion between the first and second ends of the second strap member; and
   a back strap comprising:
      a first portion comprising a tab member having a first attachment mechanism provided thereon and structured to selectively couple the first portion to the middle portion of the second strap member;

a connecting portion extending from the first portion; and a second portion coupled to a distal end of the connecting portion and having a second attachment mechanism structured to selectively couple the second portion to the first strap member or the patient sealing assembly in a manner wherein the back strap member is configured to hold the second strap member and prevent it from riding up on a head of the patient during use, wherein the tab member is structured to be threaded under the middle portion of the second strap member and bent back on itself to couple the first portion to the second strap member.

2. The back strap member according to claim 1, wherein the second portion includes first and second side strap members each being structured to be threaded under the first strap member and bent back on itself to couple the second portion to the first strap member.

3. The back strap member according to claim 2, wherein the first and second side strap members each have an arcuate shape.

4. The back strap member according to claim 2, wherein the second attachment mechanism comprises a first hook pad provided on the first side strap member and a second hook pad provided on the second side strap member.

5. The back strap member according to claim 1, wherein the second portion is structured to be directly coupled to a faceplate member or a cushion member of the patient sealing assembly.

6. A patient interface device including the patient sealing assembly and the headgear component according to claim 1.

7. A headgear component for a patient interface device structured to deliver a flow of breathing gas to a patient, comprising:
a first strap member having a first end structured to extend from a first side of a patient sealing assembly of the patient interface device and a second end structured to extend from a second side of the patient sealing assembly opposite the first side of the patient sealing assembly, the first strap member having a central portion structured to extend over a crown of the patient's head when the headgear component is donned by the patient;
a second strap member having a first end attached to the first end of the first strap member and a second end attached to the second end of the first strap member, the second strap member being structured to wrap around a back of the patient's head when the headgear component is donned by the patient, the second strap member having a middle portion between the first and second ends of the second strap member; and
a back strap comprising:
  a first portion comprising a tab member having a first attachment mechanism provided thereon and structured to selectively couple the first portion to the middle portion of the second strap member;
  a connecting portion extending from the first portion;
  a second portion coupled to a distal end of the connecting portion and having a second attachment mechanism provided thereon; and
  a clip member having a looped portion, the clip member being structured to be coupled to clothing of the patient, wherein the second portion is structured to be inserted through the looped portion and bent back on itself to couple the second portion to the clothing of the patient.

8. A patient interface device including the patient sealing assembly and the headgear component according to claim 7.

9. A headgear component for a patient interface device structured to deliver a flow of breathing gas to a patient, comprising:
a first strap member having a first end structured to extend from a first side of a patient sealing assembly of the patient interface device and a second end structured to extend from a second side of the patient sealing assembly opposite the first side of the patient sealing assembly, the first strap member having a central portion structured to extend over a crown of the patient's head when the headgear component is donned by the patient;
a second strap member having a first end attached to the first end of the first strap member and a second end attached to the second end of the first strap member, the second strap member being structured to wrap around a back of the patient's head when the headgear component is donned by the patient, the second strap member having a middle portion between the first and second ends of the second strap member; and
a back strap comprising:
  a first portion comprising a tab member having a first attachment mechanism provided thereon and structured to selectively couple the first portion to the middle portion of the second strap member;
  a connecting portion extending from the first portion; and
  a second portion coupled to a distal end of the connecting portion, wherein the second portion includes first and second side strap members each being structured to be wrapped around the neck of the patient and be coupled to one another such that the back strap member is configured to hold the second strap member and prevent it from riding up on a head of the patient during use.

10. A patient interface device including the patient sealing assembly and the headgear component according to claim 9.

11. A headgear component for a patient interface device structured to deliver a flow of breathing gas to a patient, comprising:
a first strap member having a first end structured to extend from a first side of a patient sealing assembly of the patient interface device and a second end structured to extend from a second side of the patient sealing assembly opposite the first side of the patient sealing assembly, the first strap member having a central portion structured to extend over a crown of the patient's head when the headgear component is donned by the patient;
a second strap member having a first end attached to the first end of the first strap member and a second end attached to the second end of the first strap member, the second strap member being structured to wrap around a back of the patient's head when the headgear component is donned by the patient, the second strap member having a middle portion between the first and second ends of the second strap member, the middle portion having a slit provided therein; and
a back strap comprising:
  a first portion comprising a tab member having a first attachment mechanism provided thereon and structured to selectively couple the first portion to the second strap member;
  a connecting portion extending from the first portion; and
  a second portion coupled to a distal end of the connecting portion and having a second attachment mechanism structured to selectively couple the second portion to the first strap member or the patient sealing assembly in a manner wherein the back strap member is configured to hold the second strap member and prevent it from riding up on a head of the patient during use, and wherein the tab member is structured to be threaded through the slit and bent back on itself to couple the first portion to the second strap member.

12. A patient interface device including the patient sealing assembly and the headgear component according to claim 11.

* * * * *